(12) United States Patent
Chen et al.

(10) Patent No.: US 11,230,573 B2
(45) Date of Patent: *Jan. 25, 2022

(54) HEXON PROTEIN HYPERVARIABLE REGION GENE SEQUENCE OF ADENOVIRUS AND ITS APPLICATION

(71) Applicant: JIAXING ANYU BIOTECHNOLOGY CO., LTD., Zhejiang (CN)

(72) Inventors: Ping Chen, Zhejiang (CN); Na Li, Zhejiang (CN); Xintao Zhong, Zhejiang (CN); Tingting Zhang, Zhejiang (CN); Nan Li, Zhejiang (CN)

(73) Assignee: JIAXING ANYU BIOTECHNOLOGY CO., LTD., Jiaxing (CN)

( * ) Notice: Subject to any disclaimer, the term of this patent is extended or adjusted under 35 U.S.C. 154(b) by 2 days.

This patent is subject to a terminal disclaimer.

(21) Appl. No.: 16/843,442

(22) Filed: Apr. 8, 2020

(65) Prior Publication Data
US 2020/0231631 A1    Jul. 23, 2020

Related U.S. Application Data

(63) Continuation of application No. 16/173,716, filed on Oct. 29, 2018, now Pat. No. 10,626,150.

(30) Foreign Application Priority Data

Oct. 30, 2017  (CN) .......................... 201711030114.0

(51) Int. Cl.
*C07K 14/005* (2006.01)
*C07K 16/08* (2006.01)

(52) U.S. Cl.
CPC .......... *C07K 14/005* (2013.01); *C07K 16/081* (2013.01); *C07K 2317/33* (2013.01); *C07K 2317/76* (2013.01); *C12N 2710/10022* (2013.01); *C12N 2710/10322* (2013.01); *C12N 2710/10334* (2013.01)

(58) Field of Classification Search
None
See application file for complete search history.

(56) References Cited

PUBLICATIONS

GenBank: AY046510.1. Adenoviral expression vector Ad-hiNOS, complete sequence. Dated Sep. 17, 2001.*
Rajasekhar et al. Recombinant hexon antigen based single serum dilution ELISA forrapid serological profiling against fowl adenovirus-4 causinghydropericardium syndrome in chickens. Journal of Virological Methods 207 (2014) 121-127.*
Matthews et al. Adenovirus protein-protein interactions: hexon and protein VI. Journal of General Virology (1994), 75, 3365-3374.*

\* cited by examiner

*Primary Examiner* — Nianxiang Zou
(74) *Attorney, Agent, or Firm* — NZ Carr Law Office PLLC

(57) ABSTRACT

The invention provides a gene sequence which can encode and express adenovirus hexon protein in vitro, and is represented as SEQ ID NO: 3. Also invented a protein which was translated and expressed by the gene sequence according to the invention, and the invention also relates to the use of the protein as an antigen to immunize rabbits to obtain a polyclonal antibody. The antibody mentioned above can detect adenovirus with high sensitivity and specificity.

3 Claims, 2 Drawing Sheets
Specification includes a Sequence Listing.

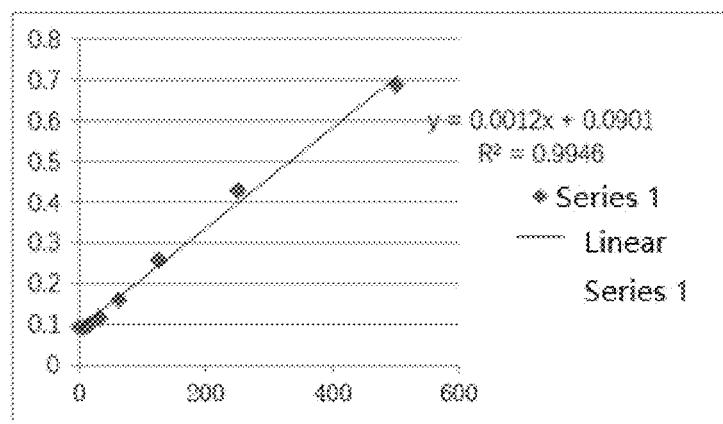
Figure 1
| Absorbance at 562nm | 0.4584 | 0.8193 | 0.4907 | 0.2553 |
|---|---|---|---|---|
| Protein concentration(n | 368.4 | 729.3 | 400.7 | 165.3 |
| Dilution times | 1 | 2 | 1 | 1 |
| volume(ml) | 1 | 1 | 1 | 1 |
| Total protein(mg) | 0.37 | 1.46 | 0.4 | 0.17 |
Figure 2
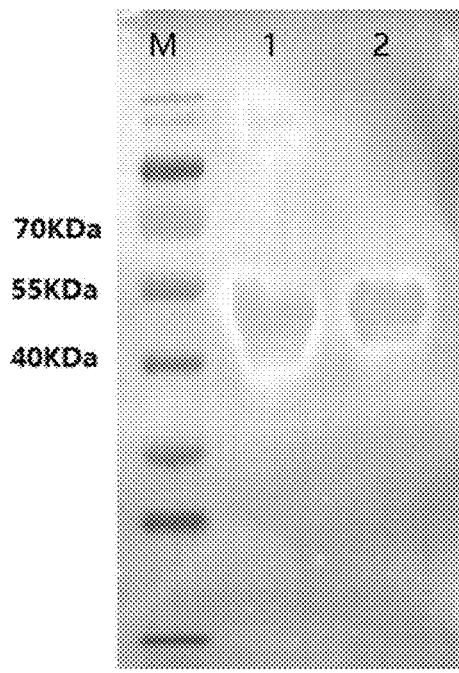
Figure 3

SEQUENCE LISTING

<160> NUMBER OF SEQ ID NOS: 4

<210> SEQ ID NO 1
<211> LENGTH: 28
<212> TYPE: DNA

<213> ORGANISM: Artificial Sequence
<220> FEATURE:
<223> OTHER INFORMATION: Primer

<400> SEQUENCE: 1
cccaagcttg aagctgctac tgctcttg                                28

<210> SEQ ID NO 2
<211> LENGTH: 32
<212> TYPE: DNA
<213> ORGANISM: Artificial Sequence
<220> FEATURE:
<223> OTHER INFORMATION: Primer

<400> SEQUENCE: 2
ccgctcgagt ttatctgaaa attctgtagc at                           32

<210> SEQ ID NO 3
<211> LENGTH: 939
<212> TYPE: DNA
<213> ORGANISM: adenovirus

<400> SEQUENCE: 3
gaagctgcta ctgctcttga aataaaccta gaagaagagg acgatgacaa cgaagacgaa    60
gtagacgagc aagctgagca gcaaaaaact cacgtatttg ggcaggcgcc ttattctggt   120
ataaatatta caaaggaggg tattcaaata ggtgtcgaag gtcaaacacc taatatgcc    180 gataaaacat ttcaacctga acctcaaata ggagaatctc agtggtacga aactgaaatt   240
aatcatgcag ctgggagagt ccttaaaaag actaccccaa tgaaaccatg ttacggttca   300
tatgcaaaac ccacaaatga aaatggaggg caaggcattc ttgtaaagca acaaaatgga   360
aagctagaaa gtcaagtgga aatgcaattt ttctcaacta ctgaggcgac cgcaggcaat   420
ggtgataact tgactcctaa agtggtattg tacagtgaag atgtagatat agaaaccccca   480 gacactcata tttcttacat gcccactatt aaggaaggta actcacgaga actaatgggc   540
caacaatcta tgcccaacag gcctaattac attgctttta gggacaattt tattggtcta   600
atgtattaca cagcacggg taatatgggt gttctggcgg gccaagcatc gcagttgaat   660
gctgttgtag atttgcaaga cagaaacaca gagctttcat accagctttt gcttgattcc   720
attggtgata gaaccaggta cttttctatg tggaatcagg ctgttgacag ctatgatcca   780
gatgttagaa ttattgaaaa tcatggaact gaagatgaac ttccaaatta ctgctttcca   840
ctgggaggtg tgattaatac agagactctt accaaggtaa aacctaaaac aggtcaggaa   900
aatggatggg aaaaagatgc tacagaattt tcagataaa                         939

<210> SEQ ID NO 4
<211> LENGTH: 313
<212> TYPE: PRT
<213> ORGANISM: Adenovirus

<400> SEQUENCE: 4

Glu Ala Ala Thr Ala Leu Glu Ile Asn Leu Glu Glu Glu Asp Asp Asp
1               5                   10                  15

Asn Glu Asp Glu Val Asp Glu Gln Ala Glu Gln Gln Lys Thr His Val
            20                  25                  30

Phe Gly Gln Ala Pro Tyr Ser Gly Ile Asn Ile Thr Lys Glu Gly Ile
        35                  40                  45

Gln Ile Gly Val Glu Gly Gln Thr Pro Lys Tyr Ala Asp Lys Thr Phe
    50                  55                  60

```
Gln Pro Glu Pro Gln Ile Gly Glu Ser Gln Trp Tyr Glu Thr Glu Ile
 65                  70                  75                  80

Asn His Ala Ala Gly Arg Val Leu Lys Lys Thr Thr Pro Met Lys Pro
                 85                  90                  95

Cys Tyr Gly Ser Tyr Ala Lys Pro Thr Asn Glu Asn Gly Gly Gln Gly
            100                 105                 110

Ile Leu Val Lys Gln Gln Asn Gly Lys Leu Glu Ser Gln Val Glu Met
            115                 120                 125

Gln Phe Phe Ser Thr Thr Glu Ala Thr Ala Gly Asn Gly Asp Asn Leu
        130                 135                 140

Thr Pro Lys Val Val Leu Tyr Ser Glu Asp Val Asp Ile Glu Thr Pro
145                 150                 155                 160

Asp Thr His Ile Ser Tyr Met Pro Thr Ile Lys Glu Gly Asn Ser Arg
                165                 170                 175

Glu Leu Met Gly Gln Gln Ser Met Pro Asn Arg Pro Asn Tyr Ile Ala
            180                 185                 190

Phe Arg Asp Asn Phe Ile Gly Leu Met Tyr Tyr Asn Ser Thr Gly Asn
        195                 200                 205

Met Gly Val Leu Ala Gly Gln Ala Ser Gln Leu Asn Ala Val Val Asp
        210                 215                 220

Leu Gln Asp Arg Asn Thr Glu Leu Ser Tyr Gln Leu Leu Leu Asp Ser
225                 230                 235                 240

Ile Gly Asp Arg Thr Arg Tyr Phe Ser Met Trp Asn Gln Ala Val Asp
                245                 250                 255

Ser Tyr Asp Pro Asp Val Arg Ile Ile Glu Asn His Gly Thr Glu Asp
            260                 265                 270

Glu Leu Pro Asn Tyr Cys Phe Pro Leu Gly Gly Val Ile Asn Thr Glu
        275                 280                 285

Thr Leu Thr Lys Val Lys Pro Lys Thr Gly Gln Glu Asn Gly Trp Glu
        290                 295                 300

Lys Asp Ala Thr Glu Phe Ser Asp Lys
305                 310
```

HEXON PROTEIN HYPERVARIABLE REGION GENE SEQUENCE OF ADENOVIRUS AND ITS APPLICATION

CROSS-REFERENCE TO RELATED APPLICATIONS

This application is a continuation of U.S. application Ser. No. 16/173,716, filed Oct. 29, 2018. U.S. application Ser. No. 16/173,716 claims priority to Chinese Application Serial No. 201711030114.0, filed Oct. 30, 2017. Each of these applications is incorporated herein by reference in their entirety.

SEQUENCE LISTING

This application is accompanied by a sequence listing both on paper and in a computer readable form that accurately reproduces the sequences described herein.

TECHNICAL FIELD

The invention relates to a gene sequence for a new adenovirus hexon protein hypervariable region, in particular to a protein expressed by the sequence, and also relates to use the protein to prepare a polyclonal antibody for detecting an adenovirus protein and the detection method.

BACKGROUND

The following background technique is used to help the reader to understand the present invention and cannot be considered as prior technique.

Adenoviruses (members of the family Adenoviridae, Ad) are a spherical double-stranded DNA virus without capsule. The diameter of adenovirus particles is 70~100 nm, and the virus capsid is icosahedral symmetric, consisting of 252 capsids, of which 240 are Hexon and 12 are penton. Adenoviruses are divided into two genera: mammalian adenovirus and avian adenovirus. At present, there are more than 100 serotypes of adenoviruses. Epitopes of hexons are the main criteria for judging different serotypes. They include the antigenic components of mammalian adenoviruses.

At present, the method for detecting adenovirus protein is to use a commercially available or prepared corresponding serotype adenovirus polyclonal antibody for the detection of adenoviral protein by Western Blot (WB). There are two methods to obtain Polyclonal antibodies: whole virus immunity and express Hexon full-protein immunization. However, there are still many problems and shortcomings of traditional reagents. The commercially available antibodies have low titer, low sensitivity and high price, and only some common serotypes are available. The whole virus preparation of adenovirus rabbit polyclonal antibodies has the disadvantages of low titer, low sensitivity, and difficulty to obtain the corresponding serologically inactivated viruses. The immunization methods for expressing Hexon full-protein due to Hexon full-protein is large, there are difficulties in expressing and purifying the protein, and which is easy to be translated incomplete, and thus the immune effect is still not satisfactory.

Since the discovery of adenovirus in 1953, there have been reports of outbreaks or epidemics of different serotype adenoviruses around the world. Most countries in the world (including China) have not established a routine detection system for adenovirus infections. Most cases of adenovirus-associated respiratory infections and diarrhea have not been diagnosed in the laboratory. Highly-specific antibodies can play a huge role in the diagnosis of adenovirus infections in laboratory diagnosis and adenovirus epidemics, and there are great requirements and application scenarios.

The adenovirus vector vaccine refers to a vaccine made by using an adenovirus as a vector and recombining the vaccine antigen gene into the virus genome so that it can express a vaccine antigen. The dose of this vaccine is small, the immunogenicity of the antigen is close to natural, the antigen does not require purification, and the vector itself can exert an adjuvant effect to enhance the immune effect. Adenovirus vectors have the characteristics of wide range of host cells, high transduction efficiency, good safety and multiple serotypes for selection. For the development and production of adenoviral vector vaccines, high efficiency specific antibodies are essential. This requires the provision of a new protein and the use of proteins to produce new antibodies to overcome the deficiencies of traditional technologies.

BRIEF SUMMARY

One side, the invention provides a Gene sequence of adenovirus hexon protein which can edit and express adenovirus hexon protein in vitro is represented as SEQ ID NO: 3. Preferably, wherein the sequence was obtained by amplifying Hexon-HVR full-length gene sequence with NCBI sequence number of AC_000008.1 and sequence was located at 19250 bp-20188 bp. Preferably, wherein the sequence of amplification primers are shown in SEQ ID NO: 1 and SEQ ID NO: 2.

In another aspect, the invention provides an adenovirus hexon protein, wherein the protein was expressed and translated in vitro by the gene sequence represented as SEQ ID NO: 3. Preferably, the translation in vitro was expressed in E. coli. Preferentially, wherein after the protein was expressed, it was purified through the following steps: i) the inclusion body which have expressed were collected by centrifuging at 8000 rpm for 10 min; ii) the obtained inclusion body was resuspended with 15 ml inclusion body washing solution, and slowly stirred at 37° C. for 30 min, then centrifuged at 4000 rpm for 30 min, and rewashing again after collecting the inclusion body pellet; iii) after centrifugation and washing twice with washing solution, the inclusion body was resuspended with 15 ml inclusion body purification solution A, slowly stirred at 37° C. for 30 min, then centrifuged at 8000 rpm for 10 min, and collecting the supernatant; iv) the supernatant was added to a well-balanced nickel column (nickel column was balanced by 3 times of column volumes of ddH$_2$O and 3 times of column volumes of inclusion body purification solution A), thoroughly mixed with the nickel column and incubated at room temperature for 30 min after closing the bottom of the nickel column; v) opening the bottom of the column, collecting the liquid which flew out from the column, and the loading was repeated for three times; vi) washing the impure protein by 5 times of column volume of the inclusion body purification solution A which containing 20 mM imidazole; vii) eluting the protein by the inclusion body purification solution A containing 250 mM imidazole, collecting protein every 1 ml and collecting 7 tubes altogether; viii) eluting the protein by the inclusion body purification solution A containing 500 mM imidazole, collecting protein every 1 ml, a total of 4 tubes were collected; ix) washing the nickel column with 3 times of column volumes of inclusion body purification solution A containing 500 mM imidazole, 3 times of column volume of ddH$_2$O and 3 times of column volume of 20% ethanol, and finally soaking the nickel column in ethanol. The inclusion body washing solution was comprised by 50 mM Tris-base, 10 mM EDTA, 100 mM NaCl and 0.5% (v/v) Triton X-100; the inclusion body purification solution A was comprised by 20 mM Tris-HCl (pH 7.9), 0.5 M NaCl, 8 M Urea and 20-500 mM Imidazole.

In another aspect, the invention provides a polyclonal antibody which was obtained by using the protein that was expressed in vitro by the gene sequence of the present invention as an antigen to immunize a rabbit.

Beneficial Effect

The invention provides a convenient source of the protein; the results can be obtained as long as there is a gene sequence of the hypervariable region of the adenovirus hexon protein.

The serotype coverage is comprehensive, however, according to most of the adenovirus serum gene sequences that reported in the current literature, many of the serotypes are difficult to obtain inactivated adenovirus or to obtain commercially available polyclonal antibodies. Furthermore, since human adenovirus 1-57 HEXON-HVR has more than 95% of the same arrangement in about 80 amino acids, the type 5 polyclonal antibody of the present invention can also detect the adenovirus 1-57 virus with about 110 KDa specific band by Western Blot. The antibody has high titer and sensitivity. Compared with ab6982, which is a commercially available adenovirus type 5 rabbit polyclonal antibody made by Abcam PLC, the result of serum antibody titer tested by ELISA shows that the antibody titer obtained by the present invention in 1:100,000 times dilution is still higher than the ab6982 in 1:5000 times dilution, and WB result shows that the antibody obtained by the present invention brings out significant brighter band than the ab6982 with the same dilution. Therefore, the antibody obtained by the present invention can not only be used for the detection of adenovirus by immunoblot assay, but also can be used for enzyme-linked immunosorbent assay to detect adenovirus. It has strong specificity, clear band in WB detection and low cost, and can greatly reduce the cost compared to the commercially available adenovirus rabbit polyclonal antibodies.

BRIEF DESCRIPTION OF THE DRAWINGS

FIG. 1 shows the standard curve.

FIG. 2 shows the results of the content of the protein after purification obtained in the present invention.

FIG. 3 shows the results of WB test using the Ad5 rabbit polyclonal antibody. Among them, M stands for Protein MAKER; 1 stands for AD5-Hexon-HVR-His protein sample pre-column nickel; 2 stands for AD5-Hexon-HVR-His protein sample post-column nickel.

DETAILED DESCRIPTION OF THE INVENTION

Figure 4:
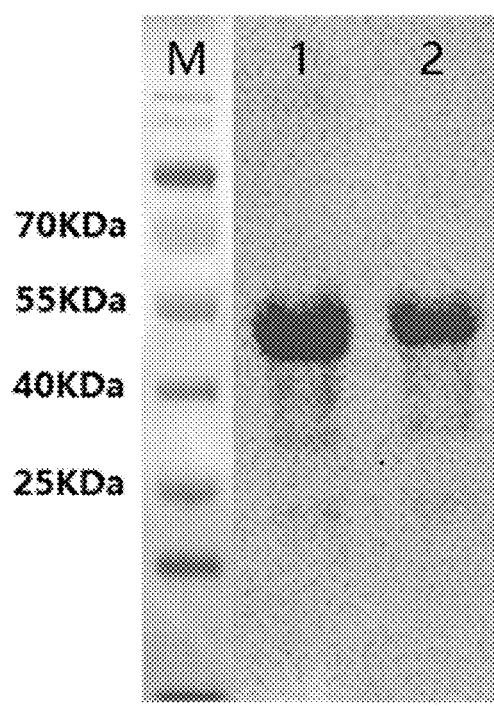
FIG. 4 shows the results of WB test using His mouse anti-monoclonal antibody. Among them, M stands for Protein MAKER; 1 stands for AD5-Hexon-HVR-His protein sample pre-column nickel; 2 stands for AD5-Hexon-HVR-His protein sample post-column nickel.
Figure 5:
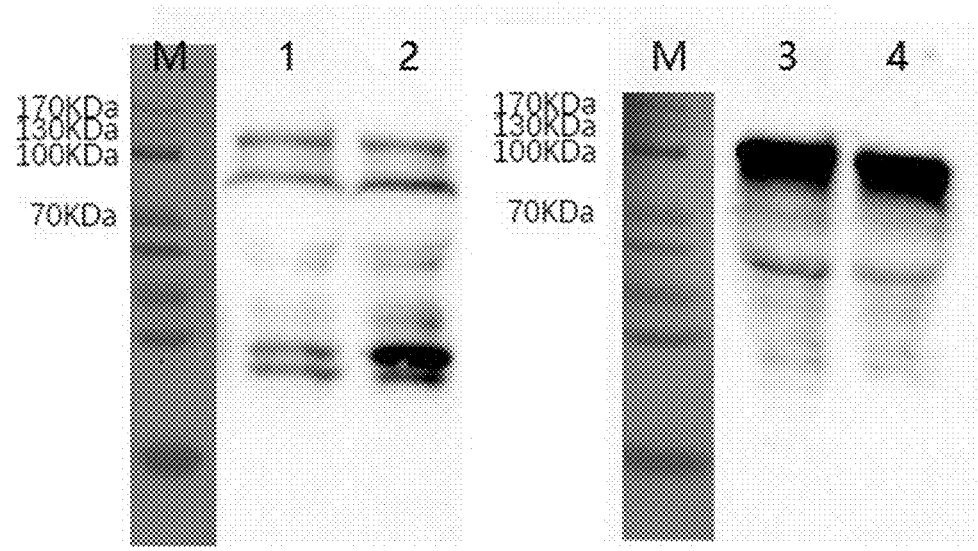
FIG. 5 shows the result of serum WB hybridization after immunization of rabbits with 293-TX cell lysate containing type 5 adenovirus as an antigen, in which M stands for protein MAKER; 1 and 2 stand for the results of purchased Ad5 multi antibody ab6982 in 1:5000 dilution; 3 and 4 stand for the results of the fourth immunizing serum of rabbit A immunized by the protein of the present invention in 1:5000 dilution.

The structures involved in the present invention or the technical terms used in the present invention are further described below. These descriptions are merely to illustrate how to implement the present invention and they cannot constitute any limitation to the present invention.

Example 1: Amplification of the AD5-Hexon-HVR Gene Sequence

A pAd/CMV/V5-DEST plasmid (purchased from ThermoFish Scientific, catalog number V49420) with adenovirus type 5 genomic DNA was used as a template for AD5-Hexon-HVR gene amplification. Designing specific primers named Ad5hexon-HVR-F/Ad5hexon-HVR-R, and using Q5 PCR MasterMix high-fidelity enzyme (purchased from Kitai, made by NEB with batch No. 0111512) to amplify the Hexon-HVR gene (Human adenovirus 5 with full-length 35881 bp and NCBI sequence number AC_000008.1, the obtained sequence position was located at 19250 bp-20188 bp). The specific operation was performed with reference to the instructions.

PCR reaction conditions are as follows:

TABLE 1

| PCR reaction conditions | | |
| --- | --- | --- |
| STEP | TEMP | TIME |
| Initial Denaturation | 98° C. | 30 seconds |
| 35 Cycles | 98° C. | 10 seconds |
|  | 56° C. | 30 seconds |
|  | 72° C. | 20 seconds |
| Final Extension | 72° C. | 2 minutes |
| Hold | 4° C. | ∞ |

Primer sequence:

```
Ad5hexon-HVR-F:
CCCAAGCTTGAAGCTGCTACTGCTCTTG          (SEQ ID NO: 1)

Ad5hexon-HVR-R:
CCGCTCGAGTTTATCTGAAAATTCTGTAGCAT      (SEQ ID NO: 2)
```

Specific reagent ratios for PCR amplification:

| Q5 High-Fidelity 2× Master Mix | 25 μL |
| --- | --- |
| F-Primer | 1 μL |
| R-Primer | 1 μL |
| pAd/CM/V5-DEST | 1 μL |
| Nuclease-Free Water | 22 μL |

The amplified product was sequenced to obtain the following sequence: AD5-Hexon-HVR gene sequence

```
                                      (SEQ ID NO: 3)
GAAGCTGCTACTGCTCTTGAAATAAACCTAGAAGAAGAGGACGATGACAA

CGAAGACGAAGTAGACGAGCAAGCTGAGCAGCAAAAAACTCACGTATTTG

GGCAGGCGCCTTATTCTGGTATAAATATTACAAAGGAGGGTATTCAAATA

GGTGTCGAAGGTCAAACACCTAAATATGCCGATAAAACATTTCAACCTGA

ACCTCAAATAGGAGAATCTCAGTGGTACGAAACTGAAATTAATCATGCAG
```

-continued
```
CTGGGAGAGTCCTTAAAAAGACTACCCCAATGAAACCATGTTACGGTTCA

TATGCAAAACCCACAAATGAAAATGGAGGGCAAGGCATTCTTGTAAAGCA

ACAAAATGGAAAGCTAGAAAGTCAAGTGGAAATGCAATTTTTCTCAACTA

CTGAGGCGACCGCAGGCAATGGTGATAACTTGACTCCTAAAGTGGTATTG

TACAGTGAAGATGTAGATATAGAAACCCCAGACACTCATATTTCTTACAT

GCCCACTATTAAGGAAGGTAACTCACGAGAACTAATGGGCCAACAATCTA

TGCCCAACAGGCCTAATTACATTGCTTTTAGGGACAATTTTATTGGTCTA

ATGTATTACAACAGCACGGGTAATATGGGTGTTCTGGCGGGCCAAGCATC

GCAGTTGAATGCTGTTGTAGATTTGCAAGACAGAAACACAGAGCTTTCAT

ACCAGCTTTTGCTTGATTCCATTGGTGATAGAACCAGGTACTTTTCTATG

TGGAATCAGGCTGTTGACAGCTATGATCCAGATGTTAGAATTATTGAAAA

TCATGGAACTGAAGATGAACTTCCAAATTACTGCTTTCCACTGGGAGGTG

TGATTAATACAGAGACTCTTACCAAGGTAAAACCTAAAACAGGTCAGGAA

AATGGATGGGAAAAAGATGCTACAGAATTTTCAGATAAA
```

The AD5-Hexon-HVR amino acid sequence deduced from the above gene sequence:

(SEQ ID NO: 4)
```
EAATALEINLEEEDDDNEDEVDEQAEQQKTHVFGQAPYSGINITKEGIQI

GVEGQTPKYADKTFQPEPQIGESQWYETEINHAAGRVLKKTTPMKPCYGS

YAKPTNENGGQGILVKQQNGKLESQVEMQFFSTTEATAGNGDNLTPKVVL

YSEDVDIETPDTHISYMPTIKEGNSRELMGQQSMPNRPNYIAFRDNFIGL

MYYNSTGNMGVLAGQASQLNAVVDLQDRNTELSYQLLLDSIGDRTRYFSM

WNQAVDSYDPDVRIIENHGTEDELPNYCFPLGGVINTETLTKVKPKTGQE

NGWEKDATEFSDK
```

Example 2 The Transformation of pET24b by AD5-Hexon-HVR Gene Sequence and Its Identification and Expression The PCR product (SEQ ID NO: 3) was double-digested by restriction enzyme XhoI and HindIII and ligated with the vector pET24b plasmid (given by Hebei Chuangyue Company, Mr. Liu Jilai) digested by the same enzyme and transformed into E. coli BL21 (purchased from TransGen Biotech Company). The positive clones were analyzed by PCR and identified by restriction enzyme digestion and nucleotide sequencing. The results indicating that the sequence of SEQ ID NO: 3 was successfully inserted into the plasmid vector and successfully transformed into the E. coli BL21

Example 3: Induced Expression of AD5-Hexon-HVR Gene

The positive strains with the correct gene sequence were inoculated in fresh LB medium and activated for expansion. The LB medium was consisted by 10 g tryptone, 5 g yeast extract, 10 g sodium chloride (NaCl), and add water to 1 L. After activation, the culture was expanded at 37° C. until the OD600 was about 0.6. The target protein expression was induced by 1 mmol/L IPTG at 37° C. for 4 h.

Example 4: Purification of Protein AD5-Hexon-HVR-His 2.1 Reagents 2.1.1 Inclusion body washing solution: 50 mM Tris-base, 10 mM EDTA, 100 mM NaCl, 0.5% (v/v) Triton X-100.

2.1.2 Inclusion body purification solution A: 20 mM Tris-HCl (pH 7.9), 0.5M NaCl, 8M Urea, 20~500 mM Imidazole.

2.2 Methods 2.2.1 The bacterial pellets were collected after centrifuging at 8000 rpm for 10 minutes.

2.2.2 The obtained inclusion body was resuspended with 15 ml inclusion body washing solution, and slowly stirred at 37° C. for 30 min, then centrifuged at 4000 rpm for 30 min, and rewashing again after collecting the inclusion body pellet.

2.2.3 After centrifugation and washing twice with washing solution, the inclusion body was resuspended with 15 ml inclusion body purification solution A, slowly stirred at 37° C. for 30 min, then centrifuged at 8000 rpm for 10 min, and collecting the supernatant.

2.2.4 The supernatant was added to a well-balanced nickel column (nickel column which was balanced by 3 times of column volumes of $ddH_2O$ and 3 times of column volumes of inclusion body purification solution A), thoroughly mixed with the nickel column and incubated at room temperature for 30 min after closing the bottom of the nickel column.

2.2.5 Opening the bottom of the column, collecting the liquid which flew out from the column, and the loading was repeated for three times.

2.2.6 Washing the impure protein by 5 times of column volume of the inclusion body purification solution A which containing 20 mM imidazole.

2.2.7 Eluting the protein by the inclusion body purification solution A containing 250 mM imidazole, collecting protein every 1 ml and collecting 7 tubes altogether.

2.2.8 Eluting the protein by the inclusion body purification solution A containing 500 mM imidazole, collecting protein every 1 ml, a total of 4 tubes were collected.

2.2.9 Washing the nickel column with 3 times of column volumes of inclusion body purification solution A containing 500 mM imidazole, 3 times of column volume of $ddH_2O$ and 3 times of column volume of 20% ethanol, and finally soaking the nickel column in ethanol.3. The concentration of the purified Ad5hexon-HVR-His protein was determined quantitatively by the BCA method.

3.1 Reagents 3.1.1 Reagent A: containing 1% BCA disodium salt, 2% anhydrous sodium carbonate, 0.16% sodium tartrate, 0.4% sodium hydroxide, and 0.95% sodium bicarbonate. Mixing the above liquid and then adjusting the pH to 11.25.

3.1.2 Reagent B: 4% copper sulfate.

3.1.3 BCA Working Solution: 100 mL Reagent A and 2 L Reagent B, and well mixed.

3.1.4 Protein standard solution: the 1.5 mg/mL bovine serum albumin standard solution was prepared by dissolving its crystals of 150 mg in 100 mL of distilled water.

3.1.5 The samples to be tested.
3.2 Operation (Table 2):

TABLE 2

Operation and Measurement Results

| Reagents (ml) | Tube number | | | | | | |
|---|---|---|---|---|---|---|---|
| | 1 | 2 | 3 | 4 | 5 | 6 | 7 |
| protein standard solution | — | 0.02 | 0.04 | 0.06 | 0.08 | 0.1 | — |
| distilled water | 0.1 | 0.08 | 0.06 | 0.04 | 0.02 | — | — |
| Purified Adenovirus Hexon Protein Hypervariable Region Protein | — | — | — | — | — | — | 0.1 |
| BCA working fluid | 2.0 | 2.0 | 2.0 | 2.0 | 2.0 | 2.0 | 2.0 |
| Protein content | | 30 | 60 | 90 | 120 | 150 | |

3.2.1 After the tubes in the above table were mixed thoroughly and incubated at 37° C. for 30 minutes, the absorbance of the solutions were measured in the wavelength of 562 nm with colorimetric method.

3.2.2 The standard curve was drawn with the protein content as the abscissa and the light absorbance as the ordinate (FIG. 1).

3.2.3 The corresponding protein content was calculated according to the absorbance value of the assay tubes and the standard curve, and then the protein concentration (g/L) in the serum was calculated.

Results: The concentration of purified Ad5hexon-HVR-His protein was quantified using the BCA method and the protein concentration was calculated according to the standard curve. After the protein concentration was measured by the BCA method, about 2.4 mg of Ad5HVR-His protein was obtained (FIG. 2).

Example 5: The Western Blot Hybridization Test was Carried Out by Using Ad5 Anti Rabbit Polyclonal Antibody and His Anti Rat Polyclonal Antibody 10 ul 5×SDS loading buffer was added to the protein solution which was obtained in example 3, and then boiling for ten minutes to make the protein denatured. Loading the sample to SDA-PAGE (the concentration of separation gel was 8%), and incubating at room temperature for 1 hour by using his antibody (purchased from ZSGB,17AW0307) and Ad5 Anti rabbit polyclonal antibody (purchased from Abcam, GR269446-1) as Primary antibodies respectively, and Goat anti-mouse (purchased from ZSGB, ZDR-5307) with 1:3000 dilutability as secondary antibody after western transfer.

As shown in FIG. 3 and FIG. 4, the results indicated that the Ad5hexon-HVR-His protein obtained was the target protein. The size of the purified product was about 50 Kd. The amino acid sequencing result revealing that the amino acid sequence of the obtained protein was 95% homologous with the predicted amino acid sequence, indicating that the amino acid of the obtained protein was the target amino acid.

Example 6: Immunizing Rabbits by the Protein Obtained in Example 4

The immune method was conducted as follows: using back muscles multi-point injection to immunize rabbits, ten points one time, and the dose are listed in the table 3.

The experimental rabbits were immunized four times following the method listed in table 3.

TABLE 3

Immunological test

| Time | work node | work content |
|---|---|---|
| Before immunization | Collecting Negative blood before immunization | Negative blood ≥0.5 ml each one |
| First immunization | First immunization | 200 µg of antigen |
| First immunization, day 14 | Second immunization | 200 µg of antigen |
| First immunization, day 28 | Third immunization | 200 µg of antigen |
| First immunization, day 42 | Forth immunization | 200 µg of antigen |
| First immunization, day 52 | Blood serum collection | Positive blood serum ≥40 ml each one |

Example 6: The Fourth Serum Antibody Titers were Detected by ELISA

Experimental Design:

6.1 Coating proteantigen: the amount of the proteantigen was 0.2 µg per hole, diluting the Ad5hexon-HVR-His protein (obtained in example 4) to 2 µg/ml with PBST solution respectively, and the protein which have been diluted were added to the ELISA96 plates with the amount of 100 µ0 per hole, then sealing the ELISA96 orifice plates and placed in 4° C. for the night.

6.2 Removing the coating solution and washing the proteantigen with PBST solution for three times. After drying, 3% BSA solution (served as sealing solution) was added to the ELISA96 plates with the amount of 50 µl per hole, and then incubating at 37° C. for 2 h.

6.3 After removing the sealing solution and drying, the ELISA96 plates were covered with membrane and conserved under −20° C. for use.

6.4 washing the ELISA plate with PBST solution for three to five times before loading samples. The dilution rates of selected serum were 1:100, 1:500, 1:2500, 1:12500, 1:25000, 1:50000, 1:100000 and 1:200000.

Negative blood serum was with the same dilution and Ad5hexon rabbit polyclonal antibody served as positive contrast was with 1:5000 dilution rate. Add PBST solution and serum to each hole according to tables 4 and 5.

6.5 adding 50 µl HRP-IgG with 1:2000 dilution to the ELISA 96 plates, and then incubating at 37° C. for 45 min.

6.6 Washing with PBST solution for three to five times, and drying.

6.7 adding 50 µl TMB Substrate to the ELISA96 plates, color developing at 37° C. for 10 to 15 minutes.

6.8 adding 50 µl stop buffer (2M $H_2SO_4$).

6.9 The corresponding OD values at 450 nm were measured.

Results are shown in tables 4 and 5; the immune serum before first immunization (negative) and after fourth immunization and fifth immunization were selected;

The immune serum of the two rabbits was selected for parallel experiments. The only difference is times of immunization.

TABLE 4

| dilut-ability | Serum of rabbit A, after three immuni-zations | Negative serum of rabbit A, after first immuni-zation | Serum of rabbit B, after three immuni-zations | Negative serum of rabbit B, before first immuni-zation | Pos-itive con-trast | PBST Blank con-trast |
|---|---|---|---|---|---|---|
| 1:10    | 0.7606 | 0.3984 | 0.723  | 0.4354 | 0.1818 | 0.0727 |
| 1:50    | 0.7352 | 0.1849 | 0.7641 | 0.1918 | 0.1494 | 0.0616 |
| 1:250   | 0.7944 | 0.083  | 0.7992 | 0.0874 | 0.1317 | 0.063  |
| 1:1250  | 0.7575 | 0.0653 | 0.7818 | 0.0671 | 0.1368 | 0.0517 |
| 1:2500  | 0.7127 | 0.0566 | 0.7208 | 0.056  | —      | 0.0774 |
| 1:5000  | 0.5933 | 0.058  | 0.6327 | 0.0538 | —      | 0.0599 |
| 1:10000 | 0.5068 | 0.0596 | 0.4987 | 0.0562 | —      | 0.0503 |
| 1:20000 | 0.3567 | 0.0568 | 0.3272 | 0.049  | —      | 0.0813 |

TABLE 5

| dilut-ability | Serum of raabblt A, after four immuni-zations | Negative serum of rabbit A, before first immuni-zation | Serum of rabbit B, after four immuni-zations | Negative serum of rabbit B, before first immuni-zation | Positive contrast | PBST blank contrast |
|---|---|---|---|---|---|---|
| 1:10    | 0.7834 | 0.118  | 0.8263 | 0.1083 | 0.2028 | 0.0576 |
| 1:50    | 0.7762 | 0.0843 | 0.8078 | 0.0784 | 0.1964 | 0.0581 |
| 1:250   | 0.7785 | 0.0755 | 0.7735 | 0.0775 | —      | 0.0633 |
| 1:1250  | 0.7291 | 0.055  | 0.6932 | 0.057  | —      | 0.0542 |
| 1:2500  | 0.5876 | 0.0766 | 0.5165 | 0.0697 | —      | 0.0539 |
| 1:5000  | 0.5463 | 0.0597 | 0.4082 | 0.0606 | —      | 0.0579 |
| 1:10000 | 0.3347 | 0.0992 | 0.266  | 0.067  | —      | 0.0591 |
| 1:20000 | 0.3016 | 0.0516 | 0.1875 | 0.0508 | —      | 0.0742 |

The results are as follows:

The results of PBST as blank control and positive contrast are corresponding with the experimental requirements, and the experimental data are reliable. The antibody titer of AD5-Hexon-HVR-His polyclonal albumen is high to 1:200000, and P/N≥2.1 after four immunizations using AD5 Rabbit polyclonal antibody (purchased from AbcamPLC with batch number GR269446-1) as positive contrast. The antibody titer of the serum from the rabbits immunized by AD5-Hexon-HVR-His protein was significantly higher than that of the positive control ADS Rabbit polyclonal antibody (abcam6982)

Example 7: The Detection of Ad5 by Western Blot Using the Serum of Rabbits Which was Immunized by AD5-Hexon-HVR-His Protein 7.1 The Antigens were 293-tx cells containing type 5 adenovirus, and the culture medium were abandoned after cell centrifugation. The supernatant was collected after cell lysis by cell lysis solution. Adding a certain amount of 5*SDS loading buffer to the supernatant and boiling for ten minutes, and then loading the sample to 15% albumen glue for electrophoresis.

7.2 Adding the serum from rabbit A after three immunizations to the positive serum immunized by AD5-Hexon-HVR-His protein, and it was diluted to 1:5000 by PBST solution. The Ad5 Rabbit polyclonal antibody (Abcam 6982) with 1:5000 dilutability was served as positive control.

The results showed that Ad5 protein can be detected in both serum and positive control serum. The Hexon band (about 110 KDa, the band 3 and 4 in picture 5) can be detected in serum with 1:5000 dilution, and which have higher brightness.

CONCLUSIONS

Both ELISA and WB results showed that the serum obtained from rabbits after four immunizations by the purified AD5-Hexon-HVR-His protein have high sensibility (more than 1:200,000 in ELISA test) and specificity (it can be used to detect Ad5hexon protein specifically). Ad5 HVR protein has good immunogenicity and can be used as a detection antibody for detection of Ad5 in future studies.

At the same time, the rabbit polyclonal antibody produced by the protein in this invention can be used to detect human adenovirus 1-57 including A, B, C, D, E adenovirus through ELISA (the specific experiments are omitted), but not all of the human adenovirus 1-57 including A, B, C, D, E adenovirus can be detected by using the control antibodies (Ad5 rabbit polyclonal antibody (Abcam 6982)). It further proved that the antibody of this invention could also help prevent the problem of failing to detect any adenovirus because of its wide detection coverage. The antibody can detect various types of adenovirus antigens with high sensitivity. The invention illustratively described herein may be practiced in the absence of any element or elements, limitation or limitations that are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by various embodiments and optional features, modification and variation of the concepts herein disclosed may be resorted to by those skilled in the art, and that such modifications and variations are considered to be within the scope of this invention as defined by the appended claims.

The content of the articles, patents, patent applications, and all other documents and electronically available information mentioned or cited herein, are hereby incorporated by reference in their entirety to the same extent as if each individual publication was specifically and individually indicated to be incorporated by reference. The applicant reserves the right to incorporate into this application any and all materials and information from any such articles, patents, patent applications or other documents.

The invention claimed is:

1. A method for producing an adenovirus hexon protein, comprising:

using two primers to amplify Hexon-HVR full-length gene sequence to get a nucleotide sequence consisting of SEQ ID NO: 3, wherein the two primers are nucleotide sequences consisting of SEQ ID NO:1 and SEQ ID NO:2;

inserting the nucleotide sequence consisting of SEQ ID NO: 3 into a plasmid vector; and transferring the vector with the nucleotide sequence consisting of SEQ ID NO: 3 into *Escherichia coli* to express said adenovirus hexon protein, wherein the Hexon-HVR full-length gene sequence is the serial number of AC 000008.1 in NCBI, and wherein the hexon protein has the amino acid sequence of SEQ ID NO: 4.

2. The method according to claim 1, wherein after the protein was expressed, it was purified by the following steps:

i) the inclusion body which was expressed was collected by centrifuging at 8000 rpm for 10 min;

ii) the obtained inclusion body was resuspended with 15 ml inclusion body washing solution, and slowly stirred at 37° C. for 30 min, then centrifuged at 4000 rpm for 30 min, and rewashed again after collecting the inclusion body pellet;

iii) after centrifugation and washing twice with washing solution, the inclusion body was resuspended with 15 ml inclusion body purification solution A, slowly stirred at 37° C. for 30 min, then centrifuged at 8000 rpm for 10 min, and collecting the supernatant;

iv) the supernatant was added to a well-balanced nickel column (nickel column was balanced by 3 times of column volumes of ddH2O and 3 times of column volumes of inclusion body purification solution A), thoroughly mixed with the nickel column and incubated at room temperature for 30 min after closing the bottom of the nickel column;

v) opening the bottom of the column, collecting the liquid which flew out from the column, and the loading was repeated for three times;

vi) washing the impure protein by 5 times of column volume of the inclusion body purification solution A containing 20 mM imidazole;

vii) eluting the protein by the inclusion body purification solution A containing 250 mM imidazole, collecting protein every 1 ml and collecting 7 tubes altogether;

viii) eluting the protein by the inclusion body purification solution A containing 500 mM imidazole, collecting protein every 1 ml, a total of 4 tubes were collected; and ix) washing the nickel column with 3 times of column volumes of inclusion body purification solution A containing 500 mM imidazole, 3 times of column volume of ddH20 and 3 times of column volume of 20% ethanol, and finally soaking the nickel column in ethanol;

wherein the inclusion body washing solution comprises 50 mM Tris-base, 10 mM EDTA, 100 mM NaCl and 0.5% (v/v) Triton X-100; and the inclusion body purification solution A comprises 20 mM Tris- HCl (pH 7.9), 0.5 M NaCl, 8 M Urea and 20-500 mM Imidazole.

3. The method according to claim 1, further comprising using the expressed protein to immunize rabbits to get an antibody.

* * * * *